(12) United States Patent
Hannant et al.

(10) Patent No.: US 7,955,572 B2
(45) Date of Patent: Jun. 7, 2011

(54) SAMPLE COLLECTION AND TESTING DEVICE WITH SWING ARM

(75) Inventors: Matthew Hannant, London (GB); Stephen J. Irwin, London (GB); Simon William Bayliff, Skipton (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 304 days.

(21) Appl. No.: 11/913,434

(22) PCT Filed: Mar. 2, 2007

(86) PCT No.: PCT/GB2007/000754
§ 371 (c)(1),
(2), (4) Date: Feb. 9, 2009

(87) PCT Pub. No.: WO2007/099355
PCT Pub. Date: Sep. 7, 2007

(65) Prior Publication Data
US 2009/0208371 A1 Aug. 20, 2009

(30) Foreign Application Priority Data
Mar. 3, 2006 (GB) .................................. 0604328.5

(51) Int. Cl.
*G01N 21/01* (2006.01)
(52) U.S. Cl. ......... 422/406; 422/401; 422/402; 422/405
(58) Field of Classification Search .......... 422/401–406, 422/58, 68.1
See application file for complete search history.

(56) References Cited

U.S. PATENT DOCUMENTS

| 5,308,580 | A | * | 5/1994 | Clark ........................... 422/419 |
| 5,869,003 | A | | 2/1999 | Nason |
| 2004/0171173 | A1 | | 9/2004 | Eckermann et al. |
| 2004/0237674 | A1 | | 12/2004 | Wu et al. |
| 2006/0018800 | A1 | * | 1/2006 | Slowey et al. ................ 422/102 |
| 2007/0015285 | A1 | * | 1/2007 | Catt et al. ........................ 436/65 |

FOREIGN PATENT DOCUMENTS
EP 0 940 678 A 9/1999
* cited by examiner

*Primary Examiner* — In Suk Bullock
*Assistant Examiner* — Timothy G Kingan
(74) *Attorney, Agent, or Firm* — Morgan, Lewis & Bockius LLP

(57) ABSTRACT

A sample collection and testing device comprising: An elongate housing (1) having a first end and a second end and a longitudinal axis; an analytical element (4) retained in the housing; a sample collector assembly extending from the first end of the housing and comprising a sample collector (24) in fluid communication with the analytical element (4); a swing arm (2) attached to the housing by a pivot fitting (44), said swing arm having proximal and distal ends; and a cap (40) at the distal end of the swing arm (2); wherein the device comprises a slide to allow limited linear movement of the cap (40) substantially along the longitudinal axis of the housing (1), and wherein the pivot fitting (44) allows the swing arm to rotate about a pivot axis substantially perpendicular to the said longitudinal axis, whereby the swing arm (2) is movable between a sample collection configuration in which the cap (40) is remote from the sample collector (24) and a sample analysis configuration in which the cap (40) encloses the sample collector (24).

10 Claims, 3 Drawing Sheets

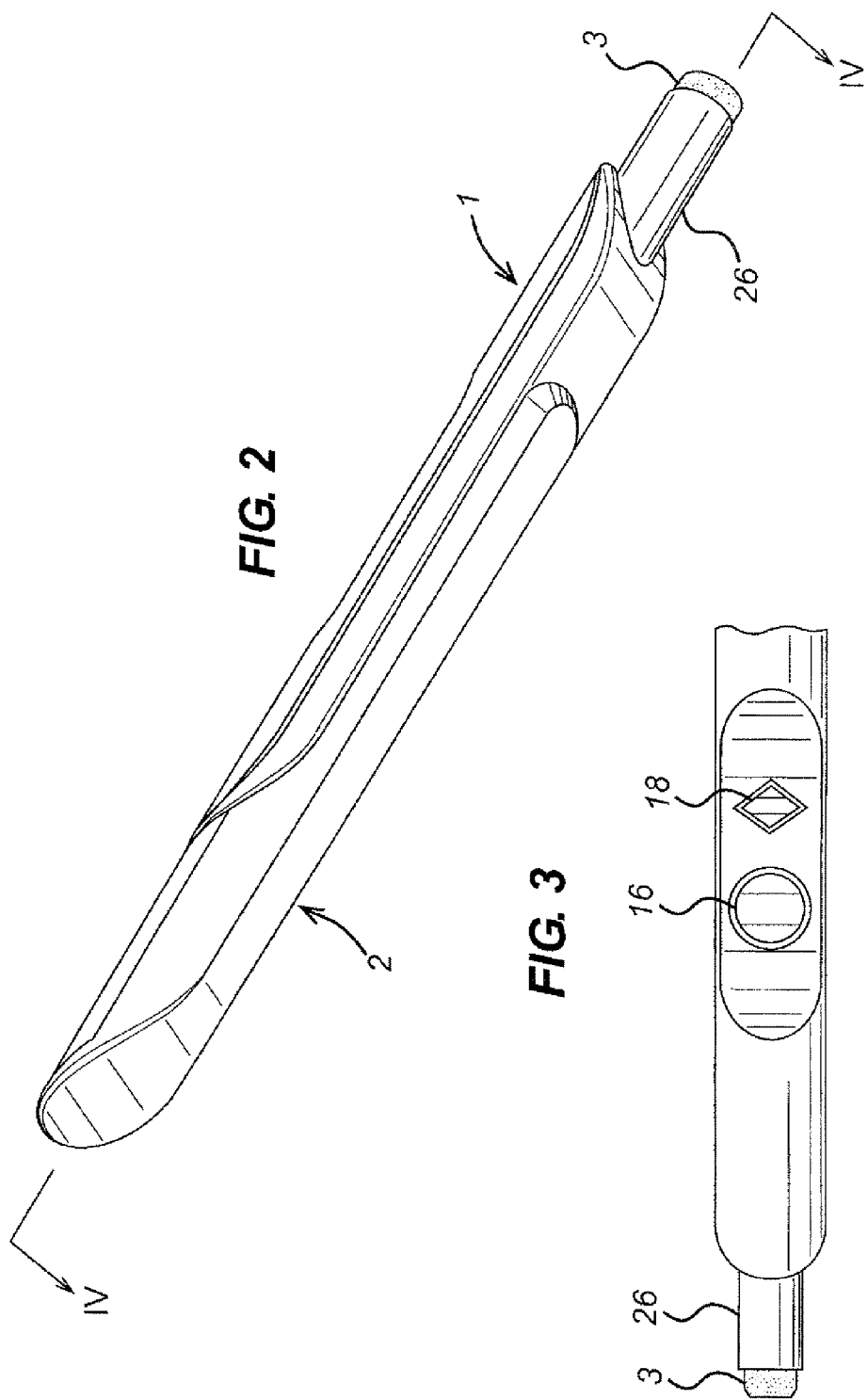

SAMPLE COLLECTION AND TESTING DEVICE WITH SWING ARM

CROSS REFERENCE TO RELATED APPLICATIONS

This application is the national stage filing of PCT Application No. PCT/GB2007/000754, filed Mar. 2, 2007 which claims priority from GB Application No. 0604328.5, filed Mar. 3, 2006.

The present invention relates to sample collection and testing devices, in particular to devices for collecting and testing biological samples such as wound fluid.

It is known to collect samples, such as biological samples, by using a sample collection device comprising a swab mounted on a shaft. Analysis of the collected sample may then be undertaken in a separate testing device, which includes a sample inlet port for receiving a sample from the swab and an analytical element capable of indicating whether the sample has tested positive for a particular predetermined analyte.

U.S. Pat. Nos. 5,266,266 and 6,248,294 describe self-contained diagnostic swab units comprising a swab mounted on a hollow shaft, and a tubular housing for receiving and storing the swab. The tubular housing further comprises a chamber containing diagnostic test reagents for analysing a sample from the swab. The distal end of the hollow shaft communicates with a reservoir of liquid, which can be expelled through the hollow shaft to flush a sample from the swab. Following collection of a sample, the swab is reinserted into the tubular housing, and the sample is flushed from the swab into the chamber for analysis.

The above devices all comprise at least two elongate parts, which are separated in use. Furthermore, the transfer of the sample from the swab to the analysis device is inefficient. It requires a relatively large amount of the wash liquid, resulting in excessive and unpredictable dilution of the sample.

According to the present invention, there is provided a sample collection and testing device comprising: an elongate housing having a first end and a second end and a longitudinal axis; an analytical element retained in the housing; a sample collector assembly extending from the first end of the housing and comprising a sample collector in fluid communication with the analytical element; a swing arm attached to the housing by a pivot fitting, said swing arm having proximal and distal ends; and a cap at the distal end of the swing arm; wherein the device comprises a slide to allow limited linear movement of the cap substantially along the longitudinal axis of the housing, and the pivot fitting allows the swing arm to rotate about a pivot axis substantially perpendicular to the said longitudinal axis, whereby the swing arm is movable between a sample collection configuration in which the cap is remote from the sample collector and a sample analysis configuration in which the cap encloses the sample collector.

Suitably, the housing further comprises a detent for releasably engaging the swing arm while it is in the sample collection configuration to retain it in said configuration. Suitably, the swing arm can be pivoted through substantially 180 degrees, whereby the swing arm in the sample collection configuration may be substantially aligned with the longitudinal axis of the housing. In these embodiments, the second end of the housing may terminate in a suitable boss onto which the cap can be pushed to retain the swing arm in alignment with the axis of the housing when the device is the sample collection configuration. The cap may be retained on the boss by a friction (interference) fit and/or by a snap fitting.

The device according to the present invention comprises a slide. The slide permits axial movement of the cap along the longitudinal axis of the housing when the swing arm is aligned with the housing, while the swing arm remains attached to the housing. This axial movement of the cap allows the cap to be pushed onto, and pulled away from, the sample collector at the first end of the housing without detaching the swing arm from the housing. The axial movement also allows the cap to be pushed onto, and pulled off, a retaining boss at the second end of the housing without detaching the swing arm from the housing. The slide may for example be provided in the swing arm. In such embodiments, the swing arm itself is extendable or retractable by means of a slide coupling between two parts of the swing arm.

In certain preferred embodiments, the slide is associated with the fitting that joins the slide arm to the housing. In these embodiments, the swing arm is suitably joined to the housing by means of a pivot that is slideably retained in a longitudinal slot in the housing or in the slide arm. The swing arm can rotate about the pivot, and the pivot can slide in the slot to allow longitudinal movement of the slide arm. The pivot may for example be a projection that is fixedly attached or integrally formed with one of the swing arm or the housing, the pivot projection being small enough to be inserted into the slot and slide freely therein. The pivot projection suitably comprises a flange to retain it in the slot and thereby prevent separation of the swing arm from the housing.

The inventive device allows a user to collect a sample and then to conduct testing on that sample within a compact, unitary hand-held device. This enables single-handed, simple and efficient operation. It also avoids the possibility of component parts of a sample collection and testing kit becoming separated from one another. Moreover, since the sample collector can be covered and enclosed by the cap on the swing arm both before use of the device, and immediately following the taking of the sample, the possibility of contamination of the sample collector before use, or contamination of the sample between the taking of a sample and the testing of that sample is reduced. Furthermore, the design of the device permits highly efficient transfer of a sample from the collector to the analytical element, as will be seen in more detail below.

The housing is an elongate housing having a principal axis. The housing may be made up of one, two, or more parts, for example assembled by snap-fitting. The housing is adapted to receive the analytical element. For example, the analytical element may be received in a chamber inside the housing. In other embodiments, the analytical element may be attached to a side of the housing.

The housing may be at least partially transparent, or may have windows provided therein, for observation of at least a zone of the analysis device that undergoes a color or fluorescence change inside the housing.

Suitably, the sample collector at the first end of the housing is a swab, that is to say a small pad of liquid-absorbent material. The swab may for example be formed from a hydrophilic foam material such as a polyurethane foam, or it may for example be a fibrous swab, including a bonded fiber material such as FILTONA (registered trade mark). In certain alternative embodiments, the sample collector may comprise a biopsy punch, a pipette, or another mechanical sampling device. The sample collector is dimensioned to fit inside the cap on the swing arm. Suitably, the sample collector comprises, or is mounted on, a fitting for forming a liquid-tight seal with the cap so that sample and wash liquid do not leak from within the cap when the swing arm is in the sample analysis position. For example, the sample collector may be mounted on a collector support that is dimensioned to form a substantially liquid-tight seal with the open end of the cap on the swing arm, thereby enclosing the collector inside the cap when the cap is pushed down over the collector in the sample analysis configuration. Suitably, the collector support is a substantially tubular projection extending from the first end of the housing. The cap may engage over the sample collector assembly by an interference (friction) fit and/or by snap-fitting, whereby application of a predetermined linear force can overcome the engagement.

The sample collector is in fluid communication with the analytical element by means of a conduit in the housing, and/or by means of a capillary transfer device such as a wick. In some embodiments, the sample collector is an elongate porous body having one end projecting for collection of the sample and a second end extending into the device for wicking the sample to the analytical element. With such arrangements, the sample may be taken up from the sample collector into the analytical element with minimum dead volume and minimum dilution of the sample.

The swing arm is likewise suitably formed from thermoplastics, for example by injection molding. The swing arm is attached to the housing by a pivot fitting. That is to say, by a fitting that allows rotation of the swing arm in about an axis substantially perpendicular to the longitudinal axis of the housing.

The swing arm has a longitudinal axis. The axis of the swing arm, when in the sample collection configuration, is suitably substantially coaxial with the principal axis of the housing. The axis of the swing arm, when in the sample analysis configuration, is suitably substantially coaxial with the principal axis of the housing. Suitably, the length of the swing arm is at least about 50% of the length of the housing, more suitably at least about 75% of said length of the housing.

As previously noted, the housing and/or the swing arm may further comprise one or more detent elements to retain the swing arm in the sample collection configuration until a predetermined minimum force is exerted to return the swing arm to the sample analysis configuration. The detents may suitably engage by interference (friction) fitting or by snap-fitting. Suitably, the swing arm can be rotated through 180 degrees from the sample analysis configuration to the sample collection configuration, such that the principal axis of the swing arm is substantially parallel to the principal axis of the elongate housing in both configurations.

Suitably, the device according to the present invention further comprises a liquid reservoir for releasing a liquid onto the sample collector when the device is in the sample analysis configuration. The liquid may have a number of functions. Primarily, it washes the sample out of the sample collector and into the analytical element. It also functions as a diluent for the sample. The solution may alternatively or additionally contain reagents for treating the sample collected by the device, for example diagnostic test reagents including immunological binding partners for selected analytes, buffers, or substrates for enzymes present in the sample. In certain embodiments the solution contains a binding partner or other inactivating agent for one or more interfering enzymes or other factors that may be present in the sample.

The liquid reservoir suitably contains from about 0.05 ml to about 1 ml of liquid, for example from about 0.1 to about 0.5 ml of liquid. It is preferably located proximate to the sample collector when the device is in the sample analysis configuration. The close proximity of the reservoir, the sample collector and the analytical element when the apparatus according to the present invention is in the analysis configuration is a significant advantage, as it minimises the amount of liquid needed to transfer the sample onto the analytical element.

In certain embodiments, the liquid reservoir is mounted on the cap attached to the swing arm, for example it may be located inside the cap. This provides a short fluid flow path from the reservoir to the sample collector when the cap is in the sample analysis position covering the sample collector.

The liquid reservoir is substantially sealed, but comprises at least one element that allows the reservoir to be opened to release the liquid onto the sample collector when the apparatus is in the analysis configuration. Suitably, the reservoir comprises a zone of weakness in fluid communication with the sample collector when the apparatus is in the analysis configuration. The reservoir may be compressible, in which case application of pressure (e.g. finger pressure) to the reservoir may be sufficient to rupture the zone of weakness and release the liquid. Alternatively or additionally, the device may comprise a projection on the housing that ruptures the zone of weakness when the cap is pressed down over the sample collector. In these or other embodiments, the reservoir may comprise an opening that is covered by a seal that can be opened by hand immediately before the apparatus is folded into the sample analysis configuration, for example a peelable sealing sheet.

The analytical element in the apparatus of the present invention may be any device that produces a detectable signal in response to one or more predetermined analytes. The signal may observable or measurable by a physical, chemical, or biological means known to those of skill in the art. A detectable signal may be a change in emission or absorbance of electromagnetic waves at a certain wavelength, hybridization or enzymatic reaction. In preferred embodiments, detectable signals are changes in colour when viewed under white light, or fluorescence when viewed under UV light. In certain embodiments, the device may be used in conjunction with an electronic sensor, for example to detect color change or fluorescence and to provide a quantitative output thereof. The electronic sensor can provide a quantitative output in digital form.

The analytical test element suitably comprises one or more diagnostic test reagents, for example immunological binding partners for selected analytes, buffers, or substrates for enzymes present in the sample.

Suitably, the analytical element contains one or more porous carrier materials. The porous carrier materials are preferably in fluid communication along substantially the whole analytical element so as to assist transfer of fluid along the device by capillary action. Suitably, the porous carrier materials are hydrophilic, but preferably they do not themselves absorb water. The porous carrier materials may function as solid substrates for attachment of reagents or indicator moieties.

The size and shape of the carrier are not critical and may vary. The carrier defines a flow path through the analytical device. Suitably, the porous carrier is in the form of one or more elongate strips or columns. In certain embodiments, the porous carrier is one or more elongate strips of sheet material, or a plurality of sheets making up in combination an elongate strip. One or more reaction zones and/or detection zones would then normally be spaced apart along the long axis of the strip. However, in some embodiments the porous carrier could, for example be in other sheet forms, such as a disk. In these cases the reaction zones and detection zones would normally be arranged concentrically around the center of the sheet, with a sample application zone in the center of the sheet. In yet other embodiments, the carrier is formed of carrier beads, for example beads made from any of the materials described above. The beads may suitably be sized from about 1 micrometer to about 1 mm. The beads may be packed into the flow path inside the housing, or may be captured or supported on a suitable porous substrate such as a glass fiber pad.

In certain embodiments, the analytical element operates on the lateral flow principle. By "lateral flow", it is meant liquid flow in which the dissolved or dispersed components of the sample are carried, preferably at substantially equal rates, and with relatively unimpaired flow, laterally through a carrier.

It will be appreciated that the devices according to the present invention may be adapted to detect more than one analyte. This can be done by the use of several different reagents in a single reaction zone, or preferably by the provision in a single device of a plurality of flow paths each adapted for detecting a different analyte. In some embodiments) the plurality of fluid flow paths are physically separated within the housing. In other embodiments multiple flow paths (lanes) can be defined in a single strip by depositing lines of wax or similar hydrophobic material between the lanes.

The devices according to the present invention may for example incorporate a bacterial sensing device of the kind described in copending application GB 0501818.9 filed on 28 Jan. 2005, the entire content of which is incorporated herein by reference.

An absorbent element may suitably be included in the devices of the present invention. The absorbent element is a means for drawing the liquid sample through the analytical element by capillary attraction. In these embodiments, the absorbent element is located proximate to the downstream end of the analytical element in the device, that is to say at the end of the element remote from the sample collector. Generally, the absorbent element will consist of a hydrophilic absorbent material such as a woven or nonwoven textile material, a filter paper or a glass fiber filter.

The device may further comprise at least one filtration element intermediate the sample collector and the analytical element to remove impurities from the sample before the sample undergoes analysis. The filtration device may for example comprise a microporous filtration sheet for removal of cells and other particulate debris from the sample.

In certain embodiments, the analytical elements according to the present invention include a control moiety in a control zone of the element, wherein the control moiety can interact with a component of the sample to improve the accuracy of the element. Suitably, the control zone is adapted to reduce false positive or false negative results. A false negative result could arise for various reasons, including (a) the sample is too dilute, or (b) the sample was too small to start with.

The sample collection and testing devices according to the present invention may be sterile, for example they may be sterilized by gamma irradiation. The devices are suitably packaged in a microorganism-impermeable container. It is envisaged that the devices according to the present invention will normally be disposable, single-use devices. For example, the housing, swing arm and liquid reservoir (where present) may all be formed from injection molded thermoplastics.

The device may be stored before use with the swing arm and cap in the said sample analysis configuration, since the cap then protects the sample collector from contamination before use. Immediately before use, the cap is pulled away from the sample collector, and the swing arm is rotated to the sample collection configuration. Alternatively, the device may be stored before use with the swing arm and cap in the sample collection configuration, in which case there may be a separate protective cover over the sample collector that is removed before use. An advantage of such a configuration is that the sample collector with its support and protective cover could be sterilized separately from the rest of the device, and then inserted into the housing during manufacture, whereby the housing and analytical device (which may be sensitive to the gamma radiation or other means used for sterilizing the sample collector) do not themselves need to be sterilized.

In use, the sample is collected, and arm is then swung into alignment with the first end of the collector following collection of the sample and engaged over the swab for the sample analysis. The liquid reservoir is then ruptured to release the liquid onto the sample collector and thereby wash the sample into the analytical element.

A specific embodiment of the present invention will now be described, by way of example, with reference to the accompanying drawings, in which:

FIG. 2 is a perspective view from below of the assembled device of FIG. 1, with the swing arm shown in a sample collection configuration;

FIG. 3 shows a partial top plan view of the first end of the assembled device of FIG. 2;

Figure 1:
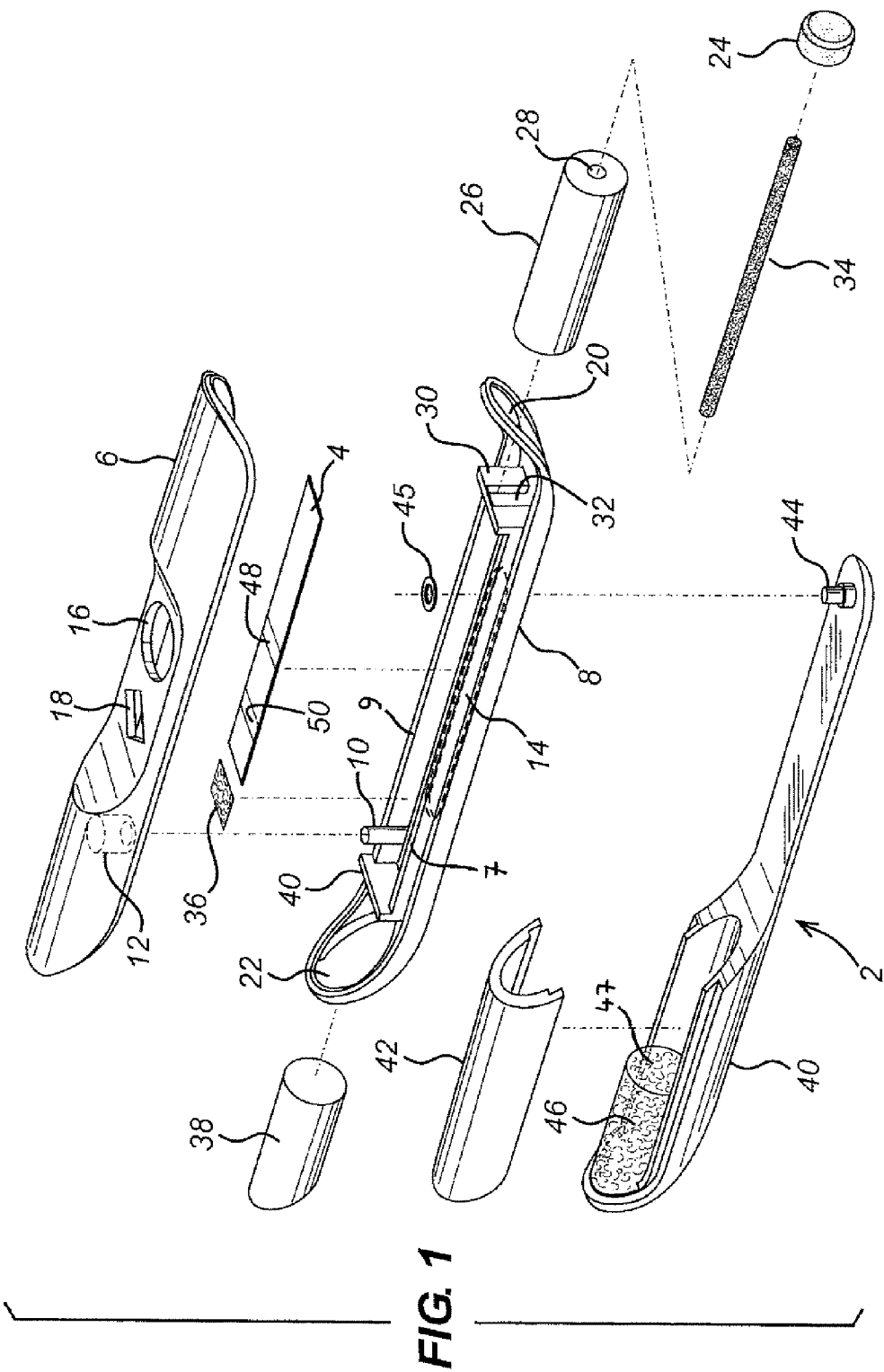
FIG. 1 is a perspective, exploded view of a sample collection and testing device in accordance with the present invention.

With reference to the accompanying drawings, a sample collection and testing device generally comprises a housing 1, a swing arm 2, a sample collector 3, and an analytical test strip 4. The housing 1 comprises a body portion formed from an upper part 6 and a lower part 8. Each housing part may be made by injection molding of thermoplastics. The parts are fitted together by means of a frictional fit between a post 10 on the lower housing part and a complementary socket 12 on the upper housing part. It will be appreciated, however, that the upper and lower housing parts could additionally or alternatively be fitted together by other means such as adhesive.

An internal chamber is defined between an upper surface of the lower housing part 8 and a lower surface of the upper housing part 6. The analytical test strip 4 is located in a longitudinal recess defined between two side walls 7,9 and two end walls 30,40 within the chamber. An absorbent strip 36 is also located in the longitudinal recess, proximate to the end wall 40 and in fluid contact with the test strip 4 to draw liquid through the test strip 4.

Upper housing part 6 has window apertures 16, 18 therein for observation of the detection zone 48 and control zone 50, respectively of the test strip 4. Lower housing part 8 has a longitudinal slot 14 in the outer wall thereof. The total length of the housing is about 10 cm. The length of slot 14 is about 5 cm. The two ends of the lower housing part 8 curve upwardly to define the end walls of the housing. Apertures 20,22 are provided in the end walls.

A sample collector assembly is inserted into aperture 20 at the first end of the housing. The sample collector assembly comprises a tubular support 26 and a swab 24 formed from an open-celled hydrophilic polyurethane foam. A first end of the tubular support 26 is inserted into aperture 20 and abuts against end wall 30 of the internal recess inside the housing. The tubular support 26 is fixed in this position by adhesive. The swab 24 is adhered to the second end of the tubular support, which projects from the housing 1.

A wick 28 formed from a hydrophilic fibrous material, is packed in the interior of the tubular support 26 to assist liquid transfer from the swab 24 to the analytical test strip 4. The wick 28 extends from the first end of the tubular support through aperture 32 in end wall 30, and into contact with the test strip 4 in order to transfer fluid from the swab 24 to the test strip 4. The second end of the tubular support 26 proximate to the swab 24 is dimensioned to form a liquid-tight friction fit with the cap 40 on the swing arm 2 when the device is in the sample analysis configuration shown in FIG. 5.

Figure 4:
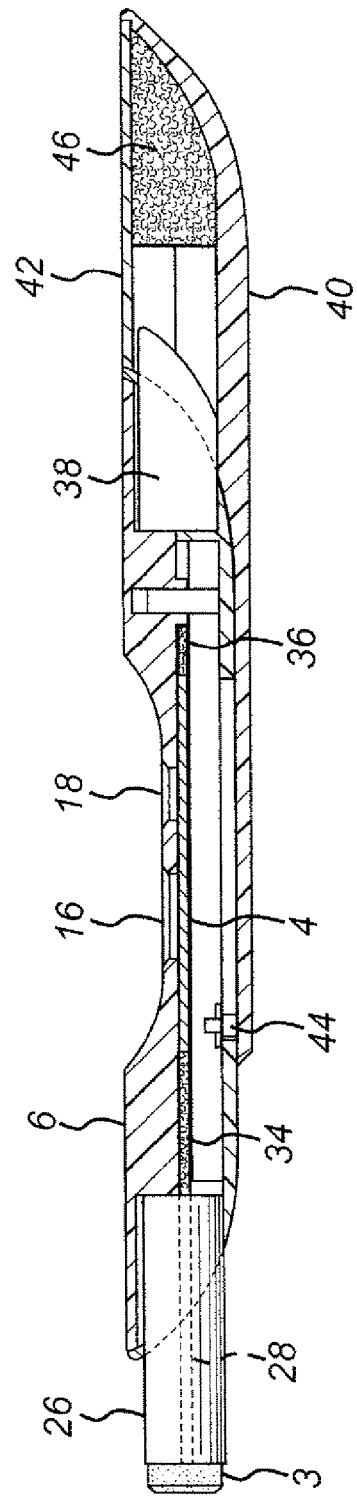
FIG. 4 shows a longitudinal cross sectional view along IV-IV in the assembled device of FIG. 2.

A cylindrical boss 38 is inserted into the aperture 22 in the second end of the housing 1 and abuts against end wall 40 of the internal recess inside the housing. The boss 38 is fixed in this position by adhesive. The projecting end of the boss 38 is dimensioned to form a friction fit with the cap 40 on the swing arm 2 when the swing arm is in the sample collection configuration, as shown in FIGS. 2 and 4.

The swing arm 2 has proximal and distal ends. The swing arm is molded separately from the housing and attached thereto by a pivot fitting. The pivot fitting comprises a cylindrical pivot projection 44 molded integrally with the proximal end of the swing arm 2. The pivot projection 44 is received in the slot 14 in the lower housing part 8, and retained therein by an annular flange 45 that is press-fitted onto the top of pivot projection 44. The pivot projection 44 and slot 14 are dimensioned to allow the pivot projection to slide substantially freely along the length of the slot 14.

The swing arm 2 further comprises a cap 40 at its distal end. The cap 40 is assembled by snap-fitting cap piece 42 onto the suitably shaped swing arm. A liquid reservoir 46 having a readily breakable end wall 47 is received in the cap 40.

The analytical test strip 4 comprises reagents capable of indicating a positive test result when testing for the desired analyte in a test sample. In this embodiment, the test strip is formed from a microporous cellulose acetate sheet and includes a detection zone 48 and a control zone 50. The detection zone 48 changes colour to indicate a positive test result. The control zone 50 changes colour to indicate that a test has been successfully completed thus to reduce the incidence of false positive results.

Operation of the device is as follows. The device is initially stored with the swing arm in the sample collection configuration as shown in FIG. 4. The swab 24 is enclosed by a protective cover (not shown) that prevents contamination of the swab. In order to use the device, a user grasps the housing and removes the protective cover from the swab 24. The swab 24 is then used to obtain a sample. One example of a sample that would be suitable for analysis in the device is wound fluid (exudate). It will be appreciated, however, that almost limitless varieties of samples could be collected and tested with the device. The samples may be biological or non-biological.

Figure 5:
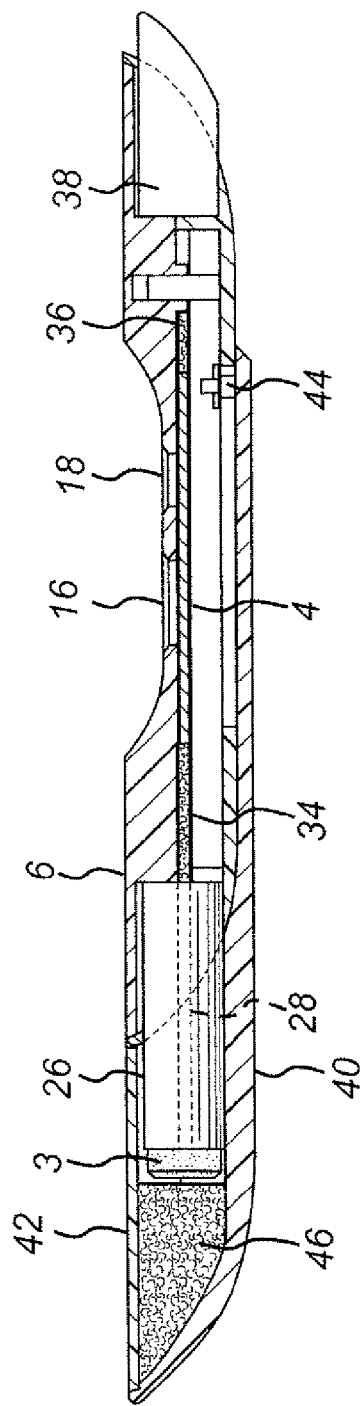
FIG. 5 shows a longitudinal cross sectional view similar to that of FIG. 4, but with the swing arm in the sample analysis configuration.

Once the sample has been collected, the user pulls the swing arm 2 linearly away from the second end of the housing to lift the cap away from the boss 38. This linear movement is made possible by the slide connection between the swing arm and the housing. The user then rotates the swing arm by about 180 degrees about the pivot until the swing arm 2 is aligned with the first end of the housing 1. The user then pushes the cap down onto the swab 24 as shown in FIG. 5. Again, this linear movement of the cap is enabled by the slide connection between the swing arm 2 and the housing 1. This results in the sample analysis configuration shown in FIG. 5. Since the swab 24 in this configuration is enclosed by the cap 40, the sample-containing swab 24 is protected from contamination, and leakage of material from the swab 24 is prevented.

Once the swing arm 2 has been moved to the sample analysis configuration the liquid reservoir 46 overlies the swab 24. The user squeezes the cap 40 to expel the solution from the reservoir into the swab 24. The liquid is drawn by capillary action along the wicking element 34 to the analysis strip 4. The solution thus carries the sample from the sample-containing swab 24 to the analytical strip, wherein the sample is tested. The absorbent element 36 helps to draw the sample through the strip 4.

The above embodiment has been described purely by way of example. It should be noted that modifications of detail may be made within the scope of the invention as defined in the accompanying claims.

The invention claimed is:

1. A sample collection and testing device comprising:
   an elongate housing having a first end and a second end and a longitudinal axis;
   an analytical element retained in the housing;
   a sample collector assembly extending from the first end of the housing and comprising a sample collector in fluid communication with the analytical element;
   a swing arm attached to the housing by a pivot fitting, said swing arm having proximal and distal ends; and
   a cap at the distal end of the swing arm;
   wherein the device comprises a slide to allow limited linear movement of the cap substantially along the longitudinal axis of the housing, and wherein the pivot fitting allows the swing arm to rotate about a pivot axis substantially perpendicular to the said longitudinal axis, whereby the swing arm is movable between a sample collection configuration in which the cap is remote from the sample collector and a sample analysis configuration in which the cap encloses the sample collector.

2. A device according to claim 1, wherein the swing arm can be pivoted through substantially 180 degrees, whereby the swing arm in said sample collection configuration is substantially aligned with said longitudinal axis with said cap located proximate to the second end of the housing.

3. A device according to claim 2, further comprising a boss projecting from said second end of the housing, onto which the cap can be fitted while it is in said sample collection configuration.

4. A device according to claim 1, wherein said slide comprises an elongate opening in the housing or in the swing arm, in which the pivot fitting is retained such that the pivot fitting can slide along the elongate opening.

5. A device according to claim 1 further including a liquid reservoir for releasing a liquid onto the sample collector when the device is in the sample analysis configuration, said liquid reservoir being located within the cap of the swing arm.

6. A device according to claim 1, wherein the sample collector is mounted on a tubular support that extends from the first end of said housing, and a liquid flow path is provided from the sample collector through said tubular support to the analytical element.

7. A device according to claim 1, wherein the cap on the swing arm forms a substantially liquid-tight enclosure around the sample collector when the device is in the sample analysis configuration.

8. A device according to claim 1, further comprising an absorbent element positioned in liquid contact with a downstream end of the analytical element to draw liquid through the analytical element from the sample collector.

9. A device according to claim 1, wherein the analytical element comprises an analytical test strip.

10. A device according to claim 1, wherein the housing includes a viewing window for viewing a portion of the analytical element.

* * * * *